(12) United States Patent
Sagoh et al.

(10) Patent No.: US 9,354,331 B2
(45) Date of Patent: May 31, 2016

(54) X-RAY COMPUTED TOMOGRAPHY APPARATUS AND RADIATION DETECTOR

(75) Inventors: Tomoe Sagoh, Utsunomiya (JP);
Michito Nakayama, Utsunomiya (JP);
Keiji Matsuda, Nasushiobara (JP);
Shuya Nambu, Nasushiobara (JP);
Atsushi Hashimoto, Yaita (JP); Takashi Kanemaru, Yaita (JP)

(73) Assignees: KABUSHIKI KAISHA TOSHIBA, Tokyo (JP); Toshiba Medical Systems Corporation, Otawara-shi (JP)

( * ) Notice: Subject to any disclaimer, the term of this patent is extended or adjusted under 35 U.S.C. 154(b) by 293 days.

(21) Appl. No.: 13/614,252

(22) Filed: Sep. 13, 2012

(65) Prior Publication Data

US 2013/0010921 A1 Jan. 10, 2013

Related U.S. Application Data

(63) Continuation of application No. PCT/JP2012/065280, filed on Jun. 14, 2012.

(30) Foreign Application Priority Data

Jun. 14, 2011 (JP) .................................. 2011-132400

(51) Int. Cl.
*A61B 6/00* (2006.01)
*G01T 1/20* (2006.01)
(Continued)

(52) U.S. Cl.
CPC ................. *G01T 1/247* (2013.01); *A61B 6/032* (2013.01); *A61B 6/4078* (2013.01);
(Continued)

(58) Field of Classification Search
CPC .. A61B 6/4208; A61B 6/4233; A61B 6/4241; G01T 1/247; G01T 1/2006; G01T 1/2008
USPC ......................... 378/98.8; 250/370.08–370.11
See application file for complete search history.

(56) References Cited

U.S. PATENT DOCUMENTS

| 7,105,828 | B2 | 9/2006 | Unger et al. |
| 7,260,174 | B2 * | 8/2007 | Hoffman ................ A61B 6/032 250/363.09 |

(Continued)

FOREIGN PATENT DOCUMENTS

| CN | 101249000 A | 8/2008 |
| CN | 102076263 A | 5/2011 |

(Continued)

OTHER PUBLICATIONS

International Search Report issued Aug. 14, 2012 in International application Serial No. PCT/JP2012/065280 filed Jun. 14, 2011.

(Continued)

*Primary Examiner* — David J Makiya
*Assistant Examiner* — Dani Fox
(74) *Attorney, Agent, or Firm* — Oblon, McClelland, Maier & Neustadt, L.L.P.

(57) ABSTRACT

According to one embodiment, an X-ray computed tomography apparatus includes an X-ray tube, a detector, a first DAS, and a second DAS. The radiation detector includes a plurality of detection elements. Each detection element repeatedly detects X-rays generated by the X-ray tube and transmitted through a subject and repeatedly generates an electrical signal corresponding to the energy of the repeatedly detected X-rays. The first DAS acquires the electrical signal detected by part of the imaging region of each detection element in the integral mode. The second DAS acquires the electrical signal detected by the other part of the imaging region of each detection element in the photon count type mode.

12 Claims, 5 Drawing Sheets

(51) Int. Cl.
G01T 1/24 (2006.01)
A61B 6/03 (2006.01)

(52) U.S. Cl.
CPC ............ *A61B 6/4208* (2013.01); *A61B 6/4233* (2013.01); *A61B 6/4241* (2013.01); *G01T 1/2006* (2013.01); *G01T 1/2008* (2013.01)

(56) References Cited

U.S. PATENT DOCUMENTS

| | | | |
|---|---|---|---|
| 7,606,347 B2 * | 10/2009 | Tkaczyk et al. | 378/19 |
| 2005/0061985 A1 | 3/2005 | Hoffman | |
| 2005/0173641 A1 | 8/2005 | Unger et al. | |
| 2006/0056581 A1 | 3/2006 | Hoffman et al. | |
| 2007/0140418 A1 | 6/2007 | Hoffman et al. | |
| 2007/0205367 A1 | 9/2007 | Deman et al. | |
| 2007/0206721 A1 | 9/2007 | Tkaczyk et al. | |
| 2007/0206722 A1 | 9/2007 | Hoffman et al. | |
| 2007/0248209 A1 | 10/2007 | Hoffman et al. | |
| 2008/0101534 A1 | 5/2008 | Ikhlef et al. | |
| 2008/0240341 A1 * | 10/2008 | Possin et al. | 378/19 |
| 2008/0304618 A1 | 12/2008 | Hoffman et al. | |
| 2009/0121142 A1 | 5/2009 | Heismann et al. | |
| 2009/0274266 A1 | 11/2009 | Sun et al. | |
| 2010/0102242 A1 * | 4/2010 | Burr et al. | 250/370.11 |
| 2011/0096892 A1 | 4/2011 | Forthmann et al. | |

FOREIGN PATENT DOCUMENTS

| | | |
|---|---|---|
| JP | 8-168482 | 7/1996 |
| JP | 2000-023965 | 1/2000 |
| JP | 2006-101926 | 4/2006 |
| JP | 2009-18154 | 1/2009 |
| JP | 2009-25308 | 2/2009 |
| JP | 2009-268892 | 11/2009 |
| WO | WO 2010/001281 A1 | 1/2010 |

OTHER PUBLICATIONS

International Written Opinion issued Aug. 14, 2012 in International application Serial No. PCT/JP2012/065280 filed Jun. 14, 2012.
International Search Report issued Aug. 14, 2012 in PCT/JP2012/065280 (English translation only).
Chinese Office Action issued Jun. 4, 2014, in China patent Application No. 201280000723.0 (with English translation).
Japanese Office Action for Application No. 2011-132400 mailed Apr. 21, 2015.
T. Ida abd Y. Iwata, Correction for counting losses in X-ray diffectometry, Journal of Applied Crystallography, 2005, 38, 426-432, URL, http://www.crl.nitech.ac.jp/ida/research/reprints/count_loss.pdf.
U.S. Appl. No. 14/813,557, Jul. 30, 2015, Tamura et al.

* cited by examiner

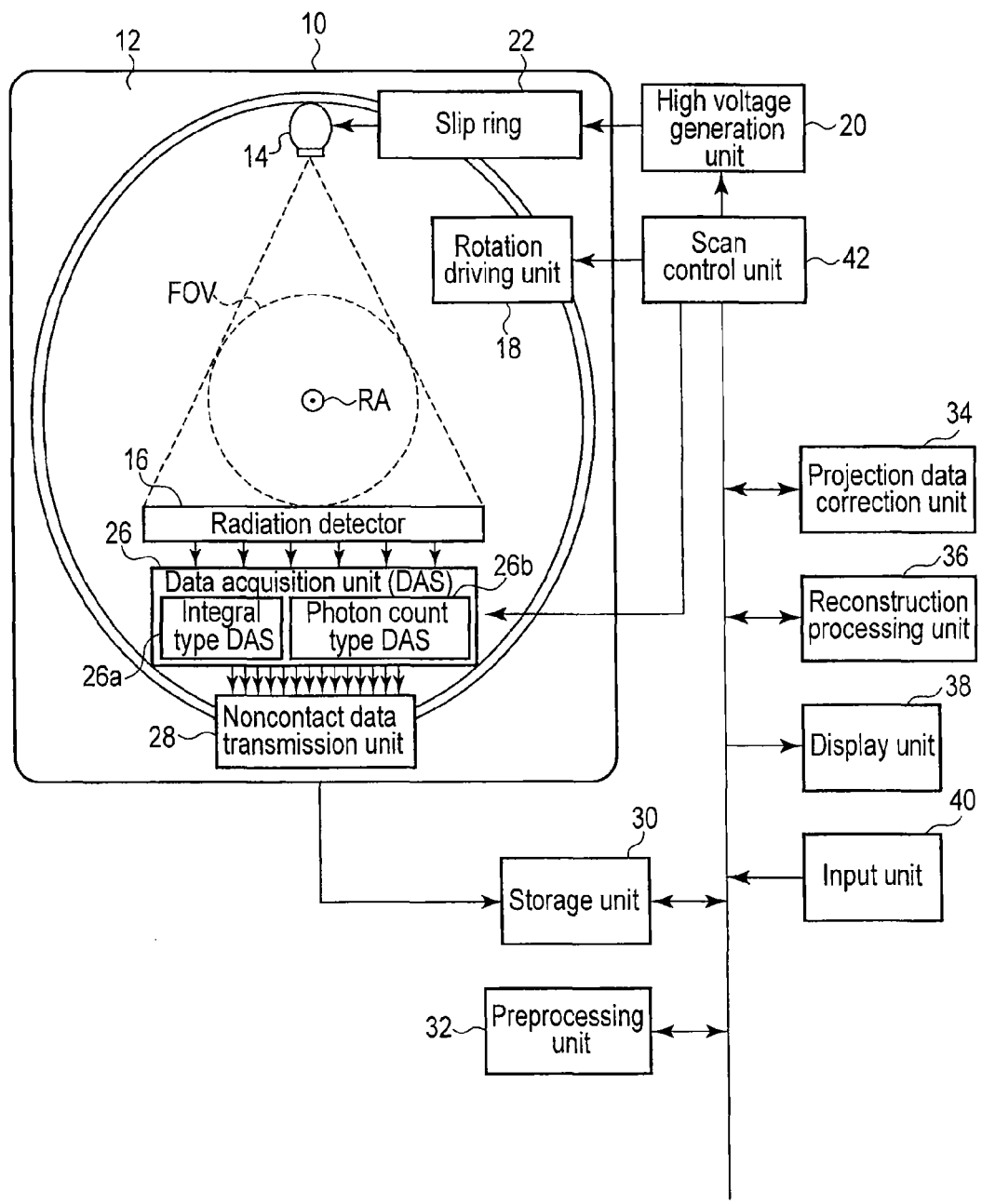
F I G. 1

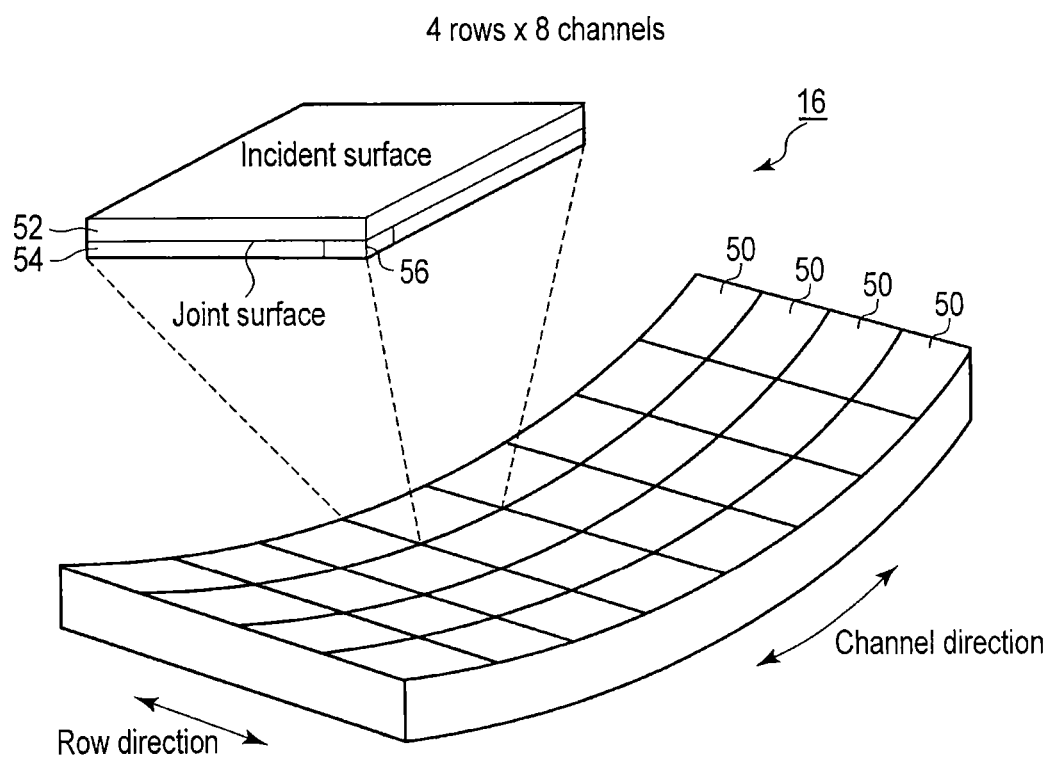
F I G. 2

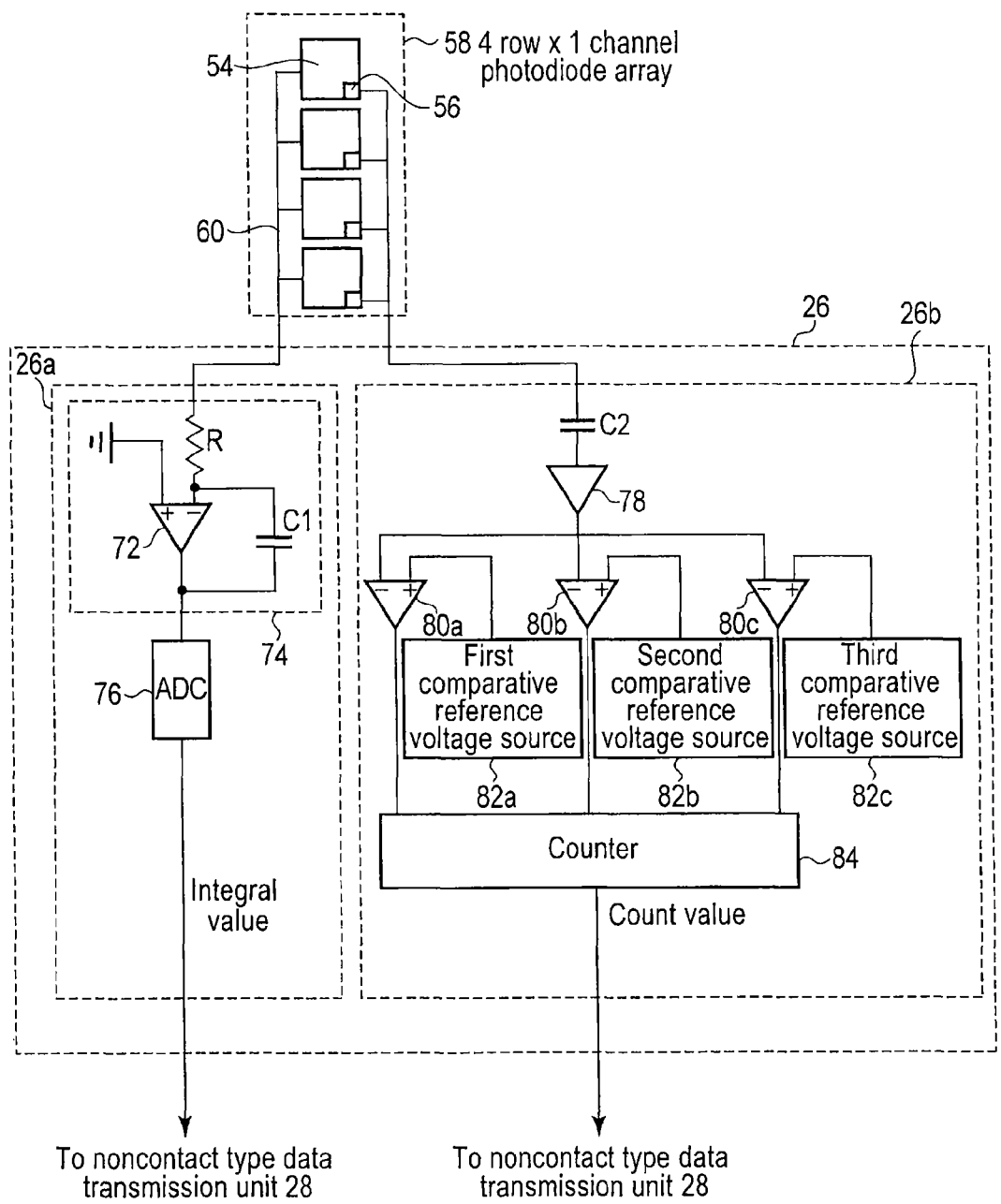
F I G. 3

X-RAY COMPUTED TOMOGRAPHY APPARATUS AND RADIATION DETECTOR

CROSS REFERENCE TO RELATED APPLICATIONS

This application is a Continuation Application of PCT Application No. PCT/JP2012/065280, filed Jun. 14, 2012 and based upon and claiming the benefit of priority from Japanese Patent Application No. 2011-132400, filed Jun. 14, 2011, the entire contents of all of which are incorporated herein by reference.

FIELD

Embodiments described herein relate generally to an X-ray computed tomography apparatus and a radiation detector.

BACKGROUND

An X-ray computed tomography apparatus irradiates a subject with X-rays using an X-ray tube, and detects X-rays transmitted through or scattered by the subject using a radiation detector. The X-ray computed tomography apparatus then acquires electrical signals from the radiation detector using a data acquisition system (DAS), and generates the data of a fluoroscopic image, tomographic image, or three-dimensional image of the subject based on the acquired electrical signals. As a DAS in a general X-ray computed tomography apparatus, a DAS in the integral mode is known.

In the integral mode, the DAS integrates electrical signals from the radiation detector for a predetermined period of time and outputs an integral signal. In the integral mode, the DAS integrates all the energies of incident X-rays, i.e., all the energies of X-rays from the low energy to the high energy. For this reason, the information of X-rays with relatively low energies becomes obscure. An image reconstructed by using such an integral signal contains artifacts due to the hardening of the quality of X-rays (a so-called beam hardening phenomenon) or decreases in the contrast resolution of a soft tissue, resulting in a deterioration in image quality.

Recently, in pursuit of new applications of an X-ray computed tomography apparatus, vigorous research and development efforts have been made on a photon count type CT which operates in the photon-counting mode. In the photon-counting mode, the DAS counts the electrical signals generated by making the radiation detector detect X-rays, and indirectly detects the count value as the number of photons of X-rays. The photon-counting mode eliminates the obscurity of low-energy information concerning the above integral mode. The photon-counting mode is lower in the maximum count rate indicating photon counting ability than the integral mode. From the viewpoint of such a photon count rate, it is difficult to apply the photon-counting mode to an X-ray computed tomography apparatus.

It is an object of an embodiment to provide an X-ray computed tomography apparatus and radiation detector which realize the photon-counting mode while maintaining high X-ray photon counting ability in the integral mode.

BRIEF DESCRIPTION OF THE DRAWINGS

FIG. 1 is a block diagram showing the arrangement of an X-ray computed tomography apparatus according to an embodiment.

FIG. 2 is a view showing the structure of a radiation detector in FIG. 1.

FIG. 3 is a view showing the detailed structure of the radiation detector and a data acquisition unit in FIG. 1.

DETAILED DESCRIPTION

Figure 4:
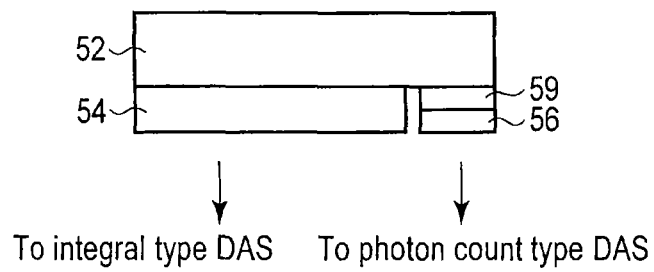
FIG. 4 is a view showing one form of a detection element of the radiation detector in FIG. 1.

In general, according to one embodiment, an X-ray computed tomography apparatus including an X-ray tube, a detector, a first acquisition unit, and a second acquisition unit. The X-ray tube is configured to generate X-rays. The detector includes a plurality of detection elements each configured to detect X-rays generated by the X-ray tube and transmitted through a subject and generate an electrical signal corresponding to an energy of the detected X-rays. The first acquisition unit is configured to acquire the electrical signal detected by part of an imaging region of each of the plurality of detection elements in an integral mode. The second acquisition unit is configured to acquire the electrical signal detected by the other part of the imaging region of each of the plurality of detection elements in a photon count type mode.

An X-ray computed tomography apparatus and radiation detector according to an embodiment will be described below with reference to the accompanying drawing.

Note that X-ray computer tomography apparatuses include a rotate/rotate-type apparatus in which an X-ray tube and a radiation detector rotate together around a subject, and a stationary/rotate-type apparatus in which many detection elements are arranged in the form of a ring, and only an X-ray tube rotates around a subject. The present embodiment is applicable to either type. In this specification, the rotate/rotate type will be exemplified.

Image reconstruction methods in the X-ray computed tomography apparatus include the full scan method and the half scan method. The full scan method requires projection data corresponding to one rotation around a subject, i.e., about 2π to reconstruct the data of a CT image of one slice. The half scan method requires projection data corresponding to it π+α[rad] (α: fan angle) to reconstruct the image data of one slice. This embodiment can be applied to both the full scan method and the half scan method. For the sake of a concrete description, the embodiment will use the full scan method.

FIG. 1 is a block diagram showing the arrangement of an X-ray computed tomography apparatus according to this embodiment. As shown in FIG. 1, the X-ray computed tomography apparatus is equipped with a gantry 10. The gantry 10 supports an annular or disk-like rotating frame 12 so as to be make it rotatable about a rotation axis RA. The rotating frame 12 includes an X-ray tube 14 and a radiation detector 16 so as to make them face each other through the subject placed on a top in an imaging region FOV. The rotating frame 12 receives the driving signals supplied from a rotation driving unit 18 and rotates the X-ray tube 14 and the radiation detector 16 at a predetermined rotational speed.

The X-ray tube 14 generates X-rays upon receiving a high voltage and a filament current from a high voltage generation unit 20 via a slip ring 22. The X-ray tube 14 generates X-rays while being rotated by the rotating frame 12.

The radiation detector 16 includes a plurality of detection elements arrayed two-dimensionally. Each detection element repeatedly detects incident X-rays and generates a current signal (electrical signal) having a charge quantity corresponding to the detected X-ray energy. A data acquisition unit 26 (to be referred to as a DAS (Data Acquisition System) hereinafter) is connected to the radiation detector 16.

FIG. 2 is a view showing an example of the structure of the radiation detector 16. As shown in FIG. 2, the radiation detector 16 includes a plurality of detection elements 50 arrayed densely in both the row direction and the channel direction. Note that the row direction coincides with the rotation axis RA direction, and the channel direction coincides with the circumferential direction around the rotation axis RA. The respective detection elements 50 are optically separated from each other by members (separators) having a light-shielding property. One detection element 50 or a set of a plurality of detection elements 50 form a read channel for the current signal. Although FIG. 2 shows the 4 row×8 channel radiation detector 16, the embodiment is not limited to this. The radiation detector 16 may include more rows and more channels.

The detection element 50 includes a scintillator 52 and two light-receiving elements 54 and 56. The scintillator 52 is formed from NaI (sodium iodide), BGO (bismuth germanium oxide), or the like. One surface of the scintillator 52 functions as an X-ray incident surface, and the two light-receiving elements 54 and 56 are provided on a surface (to be referred to as a joint surface hereinafter) on the opposite side to the incident surface.

As the light-receiving elements 54 and 56 according to this embodiment, for example, photodiodes or photomultipliers can be used. For the sake of a concrete description, assume that the light-receiving elements are photodiodes. The joint surface (imaging region) of the scintillator 52 is partitioned into the first and second sections. The first section has a larger area than the second section. The photodiode 54 is joined to the first section. The second photodiode 56 is joined to the second section. The photodiode 54 has a larger joint surface with the photodiode 54 than the second photodiode 56. The first photodiode will be referred to as the large photodiode 54. The second photodiode will be referred to as the small photodiode 56.

The photodiodes 54 and 56 and the scintillators 52 each are bonded with grease or the like. Referring to FIG. 2, the small photodiode 56 is bonded to one corner of the joint surface of the scintillator 52, and the large photodiode 54 is bonded to the remaining portion. However, the positional relationship between the large photodiode 54 and the small photodiode 56 is not limited to this, and the large photodiode 54 and the small photodiode 56 may be joined to any portions of the joint surface of the scintillator 52. For example, the small photodiode 56 may be bonded to a portion near the center of the joint surface of the scintillator 52, and the large photodiode 54 may be jointed to the remaining portion.

The scintillator 52 generates scintillation upon absorbing the energy of X-ray photons incident from the incident surface. The generated scintillation has energy corresponding to the energy of the incident X-ray photons. Each scintillation propagates in the scintillator 52 and sequentially reaches the large photodiode 54 and the small photodiode 56. The photodiodes 54 and 56 each generate a current signal having a charge quantity corresponding to the energy of scintillation having reached to itself. Note that a generated current signal is a charge pulse.

In this manner, the radiation detector 16 can detect X-rays as photons by converting incident X-rays into charge pulses. An integral type DAS 26a (to be described later) reads the charge pulses generated by the large photodiode 54. A photon count type DAS 26b (to be described later) reads the charge pulses generated by the small photodiode 26b.

The DAS 26 has a unique structure in this embodiment. The DAS 26 includes DASs of the two systems for the respective channels, i.e., the integral type DAS 26a and the photon count type DAS 26b.

The integral type DAS 26a acquires electrical signals (electrical pulses) generated by part of the region of each detection element 50 in the integral mode. More specifically, the integral type DAS 26a reads charge pulses from the detection element 50 for each channel under the control of a scan control unit 42, and integrates (adds) the read charge pulses. The integrated charge pulse will be referred to as an integral signal hereinafter. A predetermined period of time is set in accordance with the time corresponding to one view. The integral type DAS 26a generates an integral signal for each view and each channel in this manner, and converts a generated integral signal into digital data. The digitized integral signal is called raw data. A noncontact type data transmission unit 28 supplies raw data from the integral type DAS 26a to a storage unit 30 via an optical fiber cable (not shown).

In contrast, the photon count type DAS 26b acquires the electrical signals (electrical pulses) generated by the other region of each detection element 50 in the photon count type mode. More specifically, the photon count type DAS 26b reads a charge pulse from the detection element 50 for each channel under the control of the scan control unit 42. The photon count type DAS 26b specifies an energy range to which the X-ray photon absorbed by the scintillator 52 belongs among a plurality of energy ranges (windows) on the energy spectrum of X-rays based on the read charge pulse, thereby counting the number of X-ray photons in each of the plurality of energy ranges. The numbers of photons in the respective energy ranges are totalized for each channel on a view basis. The number of photons in each energy range totalized for each view will be referred to as a count value hereinafter. The noncontact type data transmission unit 28 supplies count value data from the photon count type DAS 26b to the storage unit 30 via an optical fiber cable (not shown). Note that a plurality of energy ranges are set in advance.

The storage unit 30 stores the raw data supplied from the integral type DAS 26a in association with a channel number and a view number. The storage unit 30 also stores the count value data supplied from the photon count type DAS 26b in association with a view number, a code representing an energy range, and a channel number.

A preprocessing unit 32 generates projection data in a stage immediately before image reconstruction processing by performing preprocessing such as logarithmic conversion of raw data and sensitivity correction. The storage unit 30 stores the generated projection data in association with a channel number ber view number.

A projection data correction unit 34 corrects projection data from the preprocessing unit 32 in accordance with a count value. More specifically, in order to enhance projection data concerning an energy range designated by the user, the projection data correction unit 34 multiplies projection data by the ratio between the sum of the count values in all the energy ranges and the count value concerning the energy range designated by the user. The projection data corrected by the projection data correction unit 34 will be referred to as corrected projection data hereinafter.

A reconstruction processing unit 36 reconstructs the data of a CT image concerning the subject based on corrected projection data. The CT image based on corrected projection data will be referred to as a corrected CT image hereinafter. The reconstruction processing unit 36 may also reconstruct the data of an original CT image concerning the subject based on projection data from the preprocessing unit 32. A CT image is a morphological image representing the distribution of X-ray absorption coefficients. The reconstruction processing unit 36 may reconstruct the data of a photon count image concerning the subject based on the data of a count value. A photon count image includes both a morphological image and a functional image.

A display unit 38 displays a corrected CT image, original CT image, and photon count image on a display device. The display unit 38 may superimpose a photon count image on an original CT image. As the display unit, for example, a display device such as a CRT display, liquid crystal display, organic EL display, plasma display, or the like can be used as needed.

An input unit 40 accepts various kinds of commands and information inputs which are input from the operator via an input device. More specifically, the input unit 40 inputs an energy range to be enhanced, a threshold for the segmentation of an energy range, and the like. As an input device, a keyboard, a mouse, various kinds of buttons, a touch key panel, or the like can be used as needed.

The scan control unit 42 functions as the main unit of the X-ray computed tomography apparatus. The scan control unit 42 controls the respective units in accordance with the scan conditions input via the input unit 40, and performs CT scan of the subject. At this time, the scan control unit 42 controls the DAS 26 to perform hybrid data acquisition processing which simultaneously implements both the integral mode and the photon-counting mode.

Data acquisition processing and projection data correction processing performed under the control of the scan control unit 42 will be described in detail next.

Data Acquisition Processing

FIG. 3 is a view showing the detailed structure of the radiation detector 16 and DAS 26 which are used to implement data acquisition processing. For the sake of simplicity, FIG. 3 shows only a structure corresponding to one channel. In addition, FIG. 3 shows, as the radiation detector 16, only a photodiode array 58 which is a set of photodiodes corresponding to 4 rows×1 channel. The photodiode array 58 is constituted by four large photodiodes 54 and four small photodiodes 56.

As shown in FIG. 3, each large photodiode 54 is provided with a read line 60 for charge pulses. The read lines 60 provided on the respective large photodiodes 54 are integrated into one line and connected to the integral type DAS 26a. Likewise, each small photodiode 56 is provided with a read line 62 for charge pulses. The read lines 62 provided on the respective small photodiodes 56 are integrated into one line and connected to the photon count type DAS 26b. As described above, each detection element is provided with two read lines for charge pulses.

As is well known, as the number of scintillations generated in the scintillator 52 increases, the charge pulses supplied from the photodiodes 54 and 56 overlap (pile up). As described above, since the integral type DAS 26a integrates charge pulses, the overlap of charge pulses has no influence on the accuracy of an integral value. In other words, the integral type DAS 26a has a high X-ray photon counting ability. Therefore, the larger the number of charge pulses supplied to the integral type DAS 26a, the better. On the other hand, the photon count type DAS 26b counts charge pulses while regarding them as X-ray photons, and hence the overlap of charge pulses has a great influence on the X-ray photon counting ability. In other words, the photon count type DAS 26b has a low counting ability. The number of charge pulses supplied to the photon count type DAS 26b is preferably small enough to prevent charge pulses from overlapping.

The large photodiode 54 is designed to have an area larger than the small photodiode 56 because of the above difference in counting ability between the integral type DAS 26a and the photon count type DAS 26b. More specifically, the area ratio between the large photodiode 54 and the small photodiode 56 is on the order of, for example, several thousands to several millions:one.

As shown in FIG. 4, in order to prevent piling up, a scintillation attenuation member 59 for attenuating scintillation from the scintillator 52 to the small photodiode 56 may be disposed between the small photodiode 56 and the scintillator 52. The scintillation attenuation member 59 may be made of any kind of substance as long as it can attenuate the energy of scintillation. For example, aluminum is used for the scintillation attenuation member 59.

The integral type DAS 26a and the photon count type DAS 26b will be described by referring back to FIG. 3.

The integral type DAS 26a has the same structure as that of the DAS mounted in a general X-ray computed tomography apparatus. That is, the integral type DAS 26a includes, for example, an integrator 74 constituted by a resistor R, a capacitor C1, and an amplifier 72, and an ADC (Analog-to-Digital Converter) 76. The integrator 74 integrates the charge pulses read from the four large photodiodes 54 during one view into an integral signal. The integrator 74 then supplies the generated integral signal to the ADC 76. The ADC 76 generates raw data (digital integral signal) by A/D-converting the supplied integral signal. That is, raw data is integral value data. In this manner, the integral type DAS 26a generates raw data for each view. The generated raw data is supplied to the noncontact type data transmission unit 28.

The photon count type DAS 26b includes, for example, a capacitor C2, an amplifier 78, a plurality of comparators 80, a plurality of comparative reference voltage sources 82, and a counter 84. The capacitor C2 is a smoothing capacitor which smoothes the charge pulses sequentially read from four photodiodes 62. The smoothed charge pulses are supplied to the amplifier 78. The amplifier 78 amplifies charge pulses from the capacitor C2 at a predetermined gain. The amplified charge pulses are supplied to a first comparator 80a, a second comparator 80b, and a third comparator 80c. The number of comparators 80 (and comparative reference voltage sources 82) are provided in accordance with the number of thresholds for the segmentation of energy ranges. FIG. 4 shows, for example, the three comparators 80. In this case, there are four energy ranges and three thresholds. The three comparators 80 and the three comparative reference voltage sources 82 discriminate X-ray photons into energies in the four energy ranges.

Figure 5:
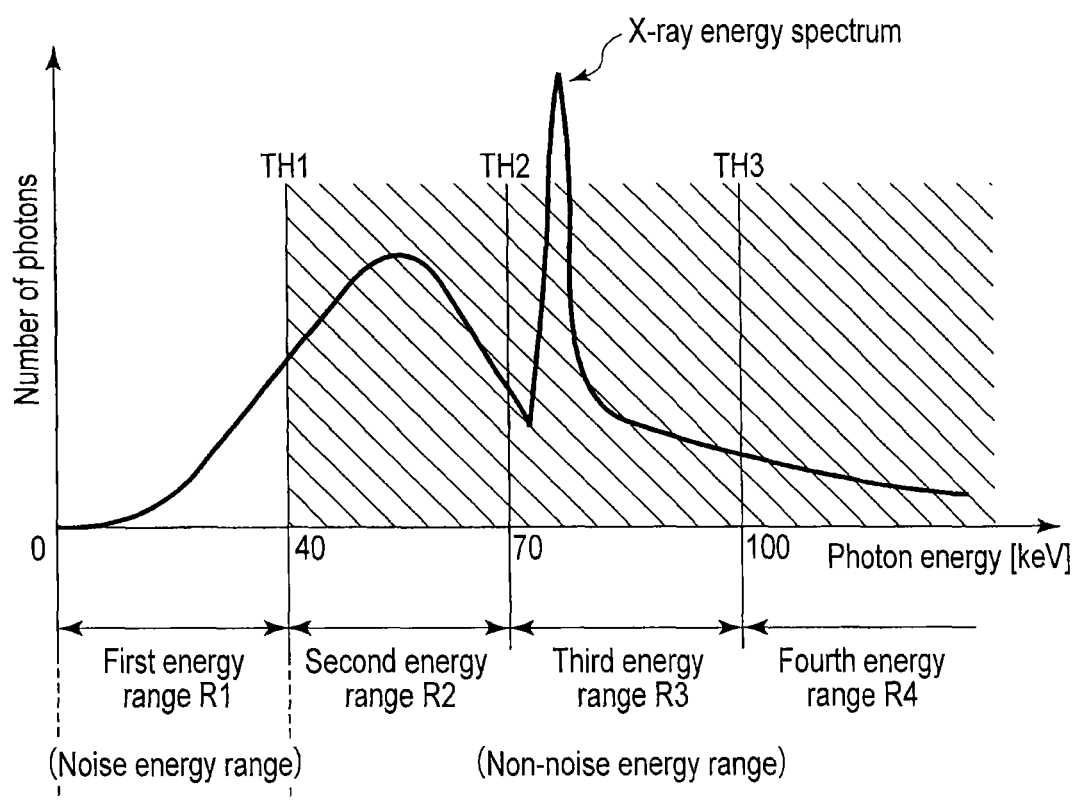
FIG. 5 is a graph showing energy ranges and thresholds which are used by a data acquisition unit in FIG. 1 in data acquisition processing.

FIG. 5 is a graph showing the relationship between a standard X-ray energy spectrum and three thresholds TH1, TH2, and TH3. Note that the ordinate and abscissa in FIG. 5 are respectively defined as the number of photons and the phone energy [keV]. As shown in FIG. 5, for energy discrimination, four energy ranges R1, R2, R3, and R4 are set by the three thresholds TH1, TH2, and TH3. The first threshold TH1 is set as a threshold for the prevention of erroneous detection so as not to detect scattered X-rays or circuit noise. The first threshold TH1 is set to a value that can discriminate the first energy range (noise energy range) R1 in which no X-ray photon can be detected, and the relatively low energy range R2. The second threshold TH2 is set to a value that can discriminate the relatively low energy range R2 and the intermediate energy range R3. The third threshold TH3 is set to a value that can discriminate the intermediate energy range R2 and the higher energy range R4. The values of the thresholds TH are empirically determined. An incident X-ray photon is discriminated to one of the first energy range R1, the second energy range R2, the third energy range R3, and the fourth energy range R4. The values of the thresholds TH1, TH2, and TH3 are set in advance via the input unit 40.

A first comparative reference voltage source 82a is connected to the first comparator 80a. The first comparative reference voltage source 82a generates the first reference voltage having a voltage value corresponding to the first threshold TH1, and supplies the voltage to the first comparator 80a. Assume that the voltage value of the first reference voltage is set in advance. The first comparator 80a compares the voltage value of a charge pulse from the amplifier 78 with a reference voltage from the first comparative reference voltage source to check the magnitude relationship between them. Note that a charge pulse has a voltage value corresponding to the energy of an incident X-ray photon. If the voltage value of the charge pulse is larger than the first reference voltage, the first comparator 80a generates a pulse having a predetermined voltage value (to be referred to as a count pulse hereinafter), and supplies it to the counter 84. If the voltage value of the charge pulse is smaller than the first reference voltage, the first comparator 80a generates no count pulse.

The second comparator 80b, a second comparative reference voltage source 82b, the third comparator 80c, and a third comparative reference voltage source 82c operate in the same manner as described above, and hence a description of the operation will be omitted. Note however that the second comparative reference voltage source 82b generates the second reference voltage, and the third comparative reference voltage source 82c generates the third reference voltage. Note that the second and third thresholds are decided in accordance with the second and third thresholds, respectively.

Figure 6:
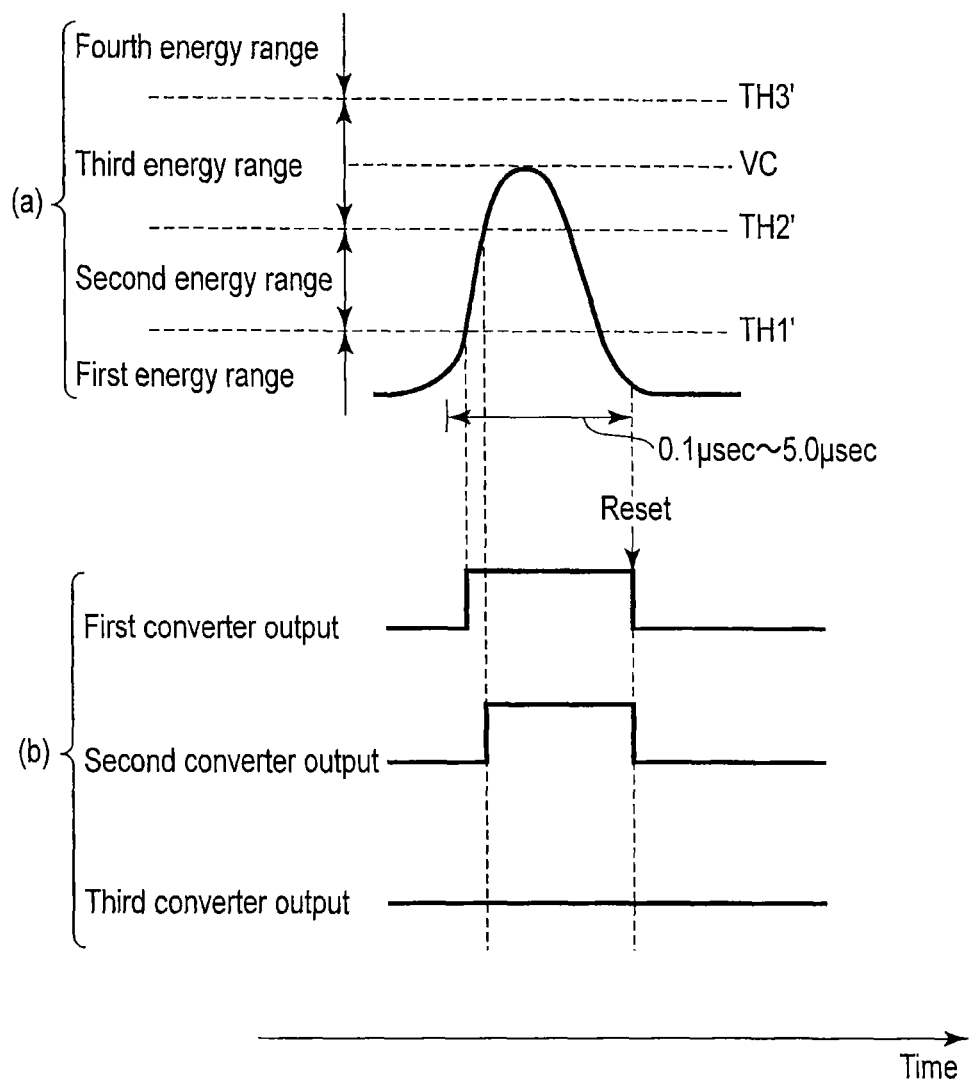
FIG. 6 is a timing chart in data acquisition processing by the data acquisition unit in FIG. 1.

FIG. 6 is a timing chart of the operation of the comparators 80. As indicated by (a) in FIG. 6, assume that the amplifier 78 has supplied a charge pulse having a voltage value VC to each comparator 80. Note that the pulse width of a charge pulse depends on the performance of a detection element. The standard pulse width is 0.1 to 5.0 μsec. The first comparative reference voltage source 82a outputs a first reference voltage TH1' obtained by converting the first threshold TH1 into a voltage. The second comparative reference voltage source 82b outputs a second reference voltage TH2' obtained by converting the second threshold TH2 into a voltage. The third comparative reference voltage source 82c outputs a third reference voltage TH3' obtained by converting the third threshold TH3 into a voltage.

Since the voltage value VC is larger than both the first reference voltage TH1' and the second reference voltage TH2', the first and second comparator 80a and 80b output count pulses and supply them to the counter 84, as indicated by (b) in FIG. 5. Since the voltage value VC is smaller than the third reference voltage TH3', the third comparator 80c outputs no count pulse.

The counter 84 specifies to which energy range the X-ray photon belongs, based on count pulses from the first, second, and third comparators 80a, 80b, and 80c.

That is, if the voltage value of a charge pulse from the amplifier 78 is equal to or less than the first reference voltage TH1', the counter 84 specifies that an X-ray photon corresponding to this charge pulse belongs to the first energy range R1. Likewise, if the voltage value of the charge pulse is between the first reference voltage TH1' and the second reference voltage TH2', the counter 84 specifies that the X-ray photon corresponding to the charge pulse belongs to the second energy range R2. If the voltage value of the charge pulse is between the second reference voltage TH2' and the third reference voltage TH3', the counter 84 specifies that the X-ray photon corresponding to the charge pulse belongs to the third energy range R3. If the voltage value of the charge pulse is equal to or more than the third reference voltage TH3', the X-ray photon corresponding to the charge pulse belongs to the fourth energy range R4.

More specifically, the counter 84 discriminates a comparator concerning the largest threshold among the thresholds set in the comparators which have supplied count pulses. By discriminating the comparator concerning the largest threshold, the counter 84 can specify to which one of the first to fourth energy ranges the X-ray photon under measurement belongs. If, for example, a count pulse is supplied from only the first comparator 80a, the X-ray photon under measurement is regarded as belonging to the second energy range. In this case, the counter 84 counts up the number of photons in the second energy range. If count pulses are supplied from the first and second comparators 80a and 80b, the X-ray photon under measurement is regarded as belonging to the third energy range. In this case, the counter 84 counts up the number of photons in the third energy range. If count pulses are supplied from the first, second, and third comparators 80a, 80b, and 80c, the X-ray photon under measurement is regarded as belonging to the fourth energy range. In this case, the counter 84 counts up the number of photons in the fourth energy range. If no pulse is supplied from any of the comparators 80, the X-ray photon under measurement is regarded as belonging to the first energy range. In this case, the counter 84 counts up the number of photons in the first energy range.

The counter 84 counts the number of photons in each energy range during one view in this manner to obtain the count value in each energy range. The data of the count value in each energy range is supplied to the noncontact type data transmission unit 28.

Projection Data Correction Processing

Projection data correction processing by the projection data correction unit 34 will be described next. In the following description, the second, third, and fourth energy ranges will be collectively referred to as a non-noise energy range, and the first energy range will be referred to as a noise energy range. That is, assume that energy ranges are classified into non-noise energy range and noise energy range, and the above first threshold is the only threshold to be used.

Projection data originating from X-ray photons belonging to a noise energy range is a cause of noise on a CT image. It is therefore possible to reduce noise on the CT image by removing projection data concerning a noise energy range from the entire projection data. For this reason, assume that a non-noise energy range is set in advance by the user via the input unit 40 as an energy range to be enhanced.

In correction processing, first of all, the projection data correction unit 34 reads out projection data concerning the same view number and channel number and the count values data in all the energy ranges from the storage unit 30. The projection data correction unit 34 then calculates the ratio between the sum of the count values in all the energy ranges and the count value in the non-noise energy range. If, for example, the ratio between the count value in the non-noise energy range and the count value in the noise energy range is 99:1, the ratio between the sum and the count value in the non-noise energy range becomes 100:99. Upon calculating the ratio, the projection data correction unit 34 multiplies the projection data with the same view number and channel number as those read out by the ratio, thereby correcting the projection data. In the above example, the projection data correction unit 34 multiplies the projection data by 99/100. In this manner, the projection data correction unit 34 generates corrected projection data by multiplying the projection data of all the views corresponding to $2\pi$ and all the channels by the ratio between the sum and the count value in the non-noise energy range. The storage unit 30 stores the corrected projection data in association with the view number and the channel number. Note that the ratio between the count value in a non-noise energy range and the count value in a noise energy range varies depending on the channel, and also varies depending the view even if the channel remains the same.

Upon performing correction processing for the projection data, the reconstruction processing unit 36 performs image reconstruction processing. In image reconstruction processing, the reconstruction processing unit 36 reads out corrected projection data corresponding to $2\pi$ from the storage unit 30 based on the view number. Of the corrected projection data corresponding to $2\pi$, the projection data of the non-noise energy range is enhanced by suppressing the projection data in the noise energy range. The data of a corrected CT image is generated by performing general image reconstruction processing such as Feldkamp reconstruction for the corrected projection data corresponding to $2\pi$. The noise on the corrected CT image has been reduced to improve the image quality.

Note that the operation of the projection data correction unit 34 can be applied to even a case in which an energy range is segmented into three or more regions as described above. In this case, it is possible to reduce beam hardening artifacts on the image by enhancing the projection data in a high energy range by correction processing. In addition, the contrast of a soft tissue on the CT image is improved by enhancing a low energy range (higher than the noise energy range and lower than the high energy range) by correction processing. Properly setting an energy range to be enhanced depending on the application in this manner can also improve the image quality of a CT image.

Note that the reconstruction processing unit 36 can reconstruct the data of a photon count image concerning a subject based on the data of a count value. The data of a count value to be used may be, for example, the data of a count value concerning all the energy ranges or the data of a count value concerning a single energy range. A photon count image based on the data of count values concerning a plurality of energy ranges indicates the energy distribution of X-ray photons on a reconstructed slice. A photon count image allows to identify the material (atomic number) of a substance on a reconstructed slice. The display unit 38 can display photon count images in different colors depending on the materials. In addition, the display unit 38 may superimpose and display a photon count image on a corrected CT image or an original CT image. Displaying a photon count image singly or superimposing and displaying it on a corrected CT image or an original CT image can provide a new image display method with clinical significance.

According to the above arrangement, the X-ray computed tomography apparatus according to this embodiment includes two photodiodes for each detection element 50, that is, the large photodiode 54 and the small photodiode 56. The charge pulses generated by the large photodiode 54 are supplied to the integral type DAS 26a to be converted into an integral signal like a general X-ray computed tomography apparatus. The integral signal is the integral of the charge pulses generated by the large photodiode 54, and is the sum of X-ray photons throughout all the energy ranges in which photons have been counted with high counting ability. The charge pulses generated by the small photodiode 56 are supplied to the photon count type DAS 26b and are converted into a count value for each energy range. The projection data correction unit 34 then assigns projection data with the ratio between the sum acquired by the photon count type DAS 26b and a count value. This makes it possible to correct the projection data as if the projection data acquired with high counting ability were discriminated according to energies by the integral type DAS 26a.

As described above, this embodiment can provide an X-ray computed tomography apparatus and radiation detector which realize the photon-counting mode while maintaining high X-ray photon counting ability in the integral mode.

According to the above description, each detection element 50 includes the scintillator 52 and the two light-receiving elements 54 and 56. However, this embodiment is not limited to this. The detection element 50 according to the embodiment may be a semiconductor detection element including a direct conversion type light-receiving element without the scintillator 52. The X-ray photon which has struck the imaging region of the direct conversion type light-receiving element is converted into electron-hole pairs. The number of electron-hole pairs generated by one incident X-ray photon depends on the energy of the incident X-ray photon. The electron-hole pairs are attracted to the electrode connected to this light-receiving element. The electrode generates an electrical pulse having a crest value corresponding to charge corresponding to each electron-hole pair. The imaging region of the direct conversion type light-receiving element is segmented into the light-receiving element 54 having an imaging region with a large area and the light-receiving element 56 having an imaging region with a small area, as in FIG. 4. The electrical pulse generated in the light-receiving element 54 is supplied to the integral type DAS 26a. The electrical pulse generated in the light-receiving element 56 is supplied to the photon count type DAS 26b. As a semiconductor material for each direct conversion type light-receiving element according to this embodiment, it is preferable to use a substance with a relatively large atomic number which can efficiently convert X-ray photons into hole-electron pairs. More specifically, CdTe, CdZnT, or the like is suitable as a semiconductor material according to this embodiment.

Modification 1

There is known a modality apparatus such as a SPECT/CT apparatus which is equipped with both a radiation detector for an integral type DAS and a radiation detector for a photon count type DAS. In a SPECT, the radiation detector detects gamma rays emitted by radioactive isotopes in a subject in the same manner as the radiation detector 16 in this embodiment detects X-rays, and generates an electrical signal corresponding to the energy of the detected gamma rays. Note that gamma rays and X-rays are classified as radiation. The radiation detector 16 according to the embodiment can function as both a detector for an integral type DAS and a detector for a photon count type DAS. The radiation detector 16 according to the embodiment can therefore integrate the radiation detectors of a SPECT/CT apparatus into one detector. In other words, the radiation detector of the CT scanner of the SPECT/CT apparatus can also serve as the radiation detector of a SPECT scanner.

Modification 2

There is known dual energy scanning which scans on the same slice while discriminating energies by changing a tube voltage or an X-ray filter and generates an electron density map or an effective atomic number map from acquired projection data. The X-ray computed tomography apparatus according to this embodiment is equipped with the radiation detector 16, the photon count type DAS 26b, and the like, and hence can discriminate energies without changing a tube voltage or an X-ray filter. The X-ray computed tomography apparatus according to the embodiment can therefore perform dual energy scanning by discriminating energies using the radiation detector 16, photon count type DAS 26b, and the like.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An X-ray computed tomography apparatus comprising:
    an X-ray tube configured to generate X-rays;
    a detector including a plurality of detection elements each configured to detect X-rays generated by the X-ray tube and transmitted through a subject and generate an electrical signal corresponding to an energy of the detected X-rays;
    a first acquisition unit configured to acquire the electrical signal detected by part of an imaging region of each of the plurality of detection elements in an integral mode; and
    a second acquisition unit configured to acquire the electrical signal detected by the other part of the imaging region of each of the plurality of detection elements in a photon count type mode,
    wherein the detector comprises:
        a scintillator configured to absorb an energy of X-rays from the X-ray tube and generate scintillation corresponding to the energy of the absorbed X-rays;
        a first light receiving element provided in a first section on one surface of the scintillator and configured to generate the electrical signal corresponding to the generated scintillation and supply the electrical signal to the first acquisition unit, and
        a second light receiving element provided in a second section other than the first section on the one surface, and the second section not overlapping with the first section in a direction perpendicular to the one surface of the scintillator, and configured to generate the electrical signal corresponding to the generated scintillation and supply the electrical signal to the second acquisition unit, and
        the first light receiving element is connected to the first acquisition unit, and the second light receiving element is connected to the second acquisition unit.

2. The X-ray computed tomography apparatus of claim 1, wherein the first section has an area larger than the second section.

3. The X-ray computed tomography apparatus of claim 1, wherein a member for attenuating the scintillation is provided between the scintillator and the second light-receiving element.

4. The X-ray computed tomography apparatus of claim 1, wherein the first acquisition unit generates an integral signal of the electrical signal, and
    the second acquisition unit repeatedly specifies an energy range to which the detected X-ray photon belongs among a plurality of preset energy ranges based on the electrical signal, and counts the number of photons in each of the plurality of energy ranges.

5. The X-ray computed tomography apparatus of claim 4, further comprising:
    a correction unit configured to correct the integral signal in accordance with the counted number of photons; and
    a reconstruction unit configured to reconstruct an image concerning the subject based on the corrected integral signal.

6. The X-ray computed tomography apparatus of claim 5, wherein the correction unit multiplies the integral signal by a ratio between the total number of photons counted in the plurality of energy ranges and the number of photons counted in a specific energy range of the plurality of energy ranges.

7. The X-ray computed tomography apparatus of claim 5, further comprising a display unit configured to display the reconstructed image.

8. The X-ray computed tomography apparatus of claim 5, further comprising:
    a first reconstruction unit configured to reconstruct a first image concerning the subject based on the integral signal; and
    a second reconstruction unit configured to reconstruct a second image concerning the subject based on the number of photons in the plurality of energy ranges.

9. The X-ray computed tomography apparatus of claim 1, wherein the detector also serves as a gamma ray detector configured to detect gamma rays from a radioactive isotope in the subject.

10. A radiation detection apparatus comprising:
    a scintillator configured to generate scintillation corresponding to an energy of incident X-rays;
    a first light-receiving element provided in a first section on one surface of the scintillator and configured to generate a first electrical signal corresponding to the generated scintillation;
    a second light-receiving element provided in a second section other than the first section on the one surface, and the second section not overlapping with the first section in a direction perpendicular to the one surface of the scintillator, and configured to generate a second electrical signal corresponding to the generated scintillation;
    a first acquisition unit configured to acquire the first electrical signal generated by the first light receiving element in an integral mode; and
    a second acquisition unit configured to acquire the second electrical signal generated by the second light receiving element in a photon count type mode,
    wherein the first light receiving element is connected to the first acquisition unit, and the second light receiving element is connected to the second acquisition unit.

11. The radiation detection apparatus of claim 10, wherein the first section has an area larger than the second section.

12. The radiation detection apparatus of claim 10, wherein a member for attenuating the scintillation is provided between the scintillator and the second light-receiving element.

* * * * *